(12) United States Patent
Shuros et al.

(10) Patent No.: US 10,729,898 B2
(45) Date of Patent: Aug. 4, 2020

(54) MULTI-SITE CRT CAPTURE VERIFICATION

(71) Applicant: Cardiac Pacemakers, Inc., St. Paul, MN (US)

(72) Inventors: Allan Charles Shuros, St. Paul, MN (US); Yinghong Yu, Shoreview, MN (US); David J. Ternes, Roseville, MN (US); Michael J. Kane, Roseville, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 575 days.

(21) Appl. No.: 15/477,635

(22) Filed: Apr. 3, 2017

(65) Prior Publication Data

US 2017/0291022 A1 Oct. 12, 2017

Related U.S. Application Data

(60) Provisional application No. 62/319,060, filed on Apr. 6, 2016.

(51) Int. Cl.
*A61N 1/00* (2006.01)
*A61N 1/365* (2006.01)
(Continued)

(52) U.S. Cl.
CPC ............... *A61N 1/00* (2013.01); *A61N 1/18* (2013.01); *A61N 1/36* (2013.01); *A61N 1/362* (2013.01);
(Continued)

(58) Field of Classification Search
CPC ............... A61N 1/00; A61N 1/18; A61N 1/36
(Continued)

(56) References Cited

U.S. PATENT DOCUMENTS

| 7,092,759 B2 | 8/2006 | Nehls et al. |
| 7,555,340 B2 | 6/2009 | Dong et al. |

(Continued)

OTHER PUBLICATIONS

Ginks, Matthew, et al., "Benefits of Endocardial and Multisite Pacing Are Dependent on the Type of Left Ventricular Electric Activation Pattern and Presence of Ischemic Heart Disease", Circ Arrhythm Electrophysiol;5, (2012), 889-897.

(Continued)

*Primary Examiner* — Nadia A Mahmood
(74) *Attorney, Agent, or Firm* — Schwegman Lundberg & Woessner, P.A.

(57) ABSTRACT

An apparatus comprises a cardiac signal sensing circuit configured for coupling electrically to a plurality of electrodes and to sense intrinsic cardiac activation at three or more locations within a subject's body using the electrodes; a stimulus circuit configured for coupling to the plurality of electrodes; a signal processing circuit electrically coupled to the cardiac signal sensing circuit and configured to determine a baseline intrinsic activation vector according to the sensed intrinsic cardiac activation; and a control circuit electrically coupled to the cardiac signal sensing circuit and stimulus circuit and configured to: initiate delivery of electrical pacing therapy using initial pacing parameters determined according to the baseline intrinsic activation vector; initiate sensing of a paced activation vector; and adjust one or more pacing therapy parameters according to the paced activation vector.

20 Claims, 7 Drawing Sheets

(51) Int. Cl.
*A61N 1/362* (2006.01)
*A61N 1/36* (2006.01)
*A61N 1/18* (2006.01)

(52) U.S. Cl.
CPC ......... *A61N 1/3622* (2013.01); *A61N 1/3627* (2013.01); *A61N 1/36578* (2013.01)

(58) Field of Classification Search
USPC ........................................................ 607/28
See application file for complete search history.

(56) References Cited

U.S. PATENT DOCUMENTS

| | | | |
|---|---|---|---|
| 7,706,879 B2 | 4/2010 | Burnes et al. | |
| 7,881,791 B2 | 2/2011 | Sambelashvili et al. | |
| 7,925,329 B2 | 4/2011 | Zdeblick et al. | |
| 8,078,276 B2 | 12/2011 | Dong et al. | |
| 8,118,751 B2 | 2/2012 | Dobak, III | |
| 8,155,739 B2 | 4/2012 | Keel et al. | |
| 8,175,703 B2 | 5/2012 | Dong et al. | |
| 8,175,707 B1 | 5/2012 | Wright et al. | |
| 8,195,292 B2 | 6/2012 | Rosenberg et al. | |
| 8,287,458 B2 | 10/2012 | Vanney et al. | |
| 8,380,308 B2 | 2/2013 | Rosenberg et al. | |
| 8,391,977 B2 | 3/2013 | Min | |
| 8,412,327 B2 | 4/2013 | Hou et al. | |
| 8,442,634 B2 | 5/2013 | Min et al. | |
| 8,478,392 B2 | 7/2013 | Sweeney et al. | |
| 8,494,631 B2 | 7/2013 | Zhang et al. | |
| 8,527,049 B2 * | 9/2013 | Koh ................ | A61B 5/0422 607/17 |
| 8,532,770 B2 | 9/2013 | Sweeney et al. | |
| 8,617,082 B2 | 12/2013 | Zhang et al. | |
| 8,639,328 B2 | 1/2014 | Hettrick et al. | |
| 8,649,853 B2 | 2/2014 | Sweeney et al. | |
| 8,649,865 B2 | 2/2014 | Bornzin et al. | |
| 8,694,093 B2 | 4/2014 | Li et al. | |
| 8,738,111 B2 | 5/2014 | Sweeney et al. | |
| 8,831,705 B2 | 9/2014 | Dobak | |
| 8,843,198 B2 | 9/2014 | Lian et al. | |
| 8,903,510 B2 | 12/2014 | Rosenberg et al. | |
| 8,914,108 B2 | 12/2014 | Bornzin et al. | |
| 8,923,965 B2 | 12/2014 | Min et al. | |
| 9,014,805 B2 | 4/2015 | Euzen et al. | |
| 9,095,718 B2 | 8/2015 | Zhang et al. | |
| 9,125,584 B2 | 9/2015 | Rosenberg et al. | |
| 9,125,585 B2 | 9/2015 | Rosenberg et al. | |
| 9,199,086 B2 | 12/2015 | Zielinski et al. | |
| 2005/0027320 A1 | 2/2005 | Nehls et al. | |
| 2006/0116581 A1 | 6/2006 | Zdeblick et al. | |
| 2006/0161211 A1 | 7/2006 | Thompson et al. | |
| 2006/0178586 A1 | 8/2006 | Dobak, III | |
| 2006/0224198 A1 | 10/2006 | Dong et al. | |
| 2008/0021336 A1 | 1/2008 | Dobak, III | |
| 2008/0058656 A1 | 3/2008 | Costello et al. | |
| 2008/0183072 A1 | 7/2008 | Robertson et al. | |
| 2008/0242976 A1 | 10/2008 | Robertson et al. | |
| 2008/0269823 A1 | 10/2008 | Burnes et al. | |
| 2009/0248103 A1 | 10/2009 | Sambelashvili et al. | |
| 2009/0254140 A1 | 10/2009 | Rosenberg et al. | |
| 2009/0264949 A1 | 10/2009 | Dong et al. | |
| 2009/0270741 A1 | 10/2009 | Vanney et al. | |
| 2009/0318995 A1 | 12/2009 | Keel et al. | |
| 2010/0023078 A1 | 1/2010 | Dong et al. | |
| 2010/0049063 A1 | 2/2010 | Dobak, III et al. | |

OTHER PUBLICATIONS

Sohal, Manav, et al., "Mechanistic insights into the benefits of multisite pacing in cardiacresynchronizationtherapy: The importance of electrical substrate and rate of left ventricular activation", Heart Rhythm Society, (2015), 2449-2457.

Sweeney, Michael, et al., "Analysis of Ventricular Activation Using Surface Electrocardiography to Predict Left Ventricular Reverse Volumetric Remodeling During Cardiac Resynchronization Therapy", Circulation. 2010;121:626-634, (2010), 626-634.

Van Deursen, Caroline, et al., "Vectorcardiography for Optimization of Stimulation Intervals in Cardiac Resynchronization Therapy", J. of Cardiovasc. Trans. Res. (2015) 8:128-137, (2015), 128-137.

* cited by examiner

MULTI-SITE CRT CAPTURE VERIFICATION

CLAIM OF PRIORITY

This application claims the benefit of priority under 35 U.S.C. § 119(e) of U.S. Provisional Patent Application Ser. No. 62/319,060, filed on Apr. 6, 2016, which is herein incorporated by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices also include wearable medical devices such as wearable cardioverter defibrillators (WCDs). WCDs are monitors that include surface electrodes. The surface electrodes are arranged to provide one or both of monitoring surface electrocardiograms (ECGs) and delivering cardioverter and defibrillator shock therapy.

Some medical devices include one or more sensors to monitor different physiologic aspects of the patient. For example, the devices may derive measurements associated with a cardiac depolarization of the patient. Such monitoring devices can be implantable or wearable and the measurements can provide useful information concerning the cardiac health of the patient.

By monitoring cardiac signals indicative of expansions or contractions, IMDs can detect abnormally slow heart rate, or bradycardia. In response to an abnormally slow heart rate some CFM devices deliver electrical pacing stimulation energy to induce cardiac depolarization and contraction. The pacing stimulation energy is delivered to provide a depolarization rate that improves hemodynamic function of the patient. Delivery of pacing therapy should be optimized to ensure therapy delivery and yet avoid unnecessary stress on the heart and unnecessary reduction of battery life. Optimal selection of the site for delivery of the pacing therapy can be part of pacing therapy optimization. Optimal site selection can lead to optimized use of pacing energy and to improved hemodynamic function of the patient or subject.

OVERVIEW

This document relates generally to systems, devices, and methods that provide electrical pacing therapy to the heart of a patient or subject. In particular it relates to, systems, devices, and methods that determine the preferred site or sites of the heart to provide pacing therapy.

An apparatus example includes a cardiac signal sensing circuit configured for coupling to a plurality of electrodes and to sense intrinsic cardiac activation at three or more locations within a subject's body using the electrodes; a stimulus circuit configured for coupling to the plurality of electrodes; a signal processing circuit electrically coupled to the cardiac signal sensing circuit and configured to determine a baseline intrinsic activation vector for the heart chamber according to the sensed intrinsic cardiac activation, wherein an intrinsic activation vector includes direction information of propagation of activation of cardiac tissue; and a control circuit electrically coupled to the cardiac signal sensing circuit and stimulus circuit and configured to: initiate delivery of electrical pacing therapy to the heart chamber using initial pacing parameters determined according to the baseline intrinsic activation vector; initiate sensing of a paced activation vector; and adjust one or more pacing therapy parameters according to the paced activation vector.

The sensing of the intrinsic activation vector and paced activation vector can provide for improved multi-site pacing therapy, as will be discussed subsequently. The pacing systems described herein use multiple available electrodes to determine the activation propagation vectors. The vectors can be used to map the patient's cardiac tissue activation to optimize the pacing therapy parameters.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Cardiac resynchronization therapy (CRT) is typically delivered to the ventricles to better synchronize the timing of depolarizations between ventricles. The induced cardiac depolarization and contraction is sometimes called capture of the heart, or cardiac capture. However, there can be a significant amount of variability in response to CRT, with some patients less likely to respond to conventional bi-ventricular (bi-V) pacing therapy than others. This may be because there can be considerable heterogeneity in the myocardial substrate of patients prescribed CRT. For example, there can be considerable variation in the etiology of heart failure and in the location of conduction block within the heart. Those patients with ischemic etiologies of heart failure and patients that exhibit narrow QRS complexes may be less likely to respond to conventional bi-V pacing strategy.

As explained previously, pacing therapy should be optimized for a patient. This can include optimizing one or both of the pacing site (or sites) and the pacing energy provided by the therapy. The pacing sites selected to deliver the pacing stimuli can have a significant impact on the therapy, but the pacing sites that are optimum for a patient may be at least partially determined by the etiology of the heart failure of the patient. Different heart failure etiology and different locations of conduction block can cause different intrinsic propagation patterns for activation of myocardial substrate in different patients. Knowledge of the activation propagation patterns can help determine the pacing sites or sites for the patient The activation propagation patterns can also help determine timing for delivering the pacing therapy. For instance, if a patient has a line of conduction block or a conduction block due to an ischemic scar, the patient may benefit from delivering pacing therapy to multiple sites (multi-site pacing or multi-point pacing) to coordinate the cardiac depolarization and resulting cardiac contraction of the patient. If the patient has a propagation pattern that is diffuse, the patient may benefit from single site pacing or limited site pacing to pre-excite the regions of slower or later depolarization. If the patient has a propagation pattern that is focal to particular region, the patient may also indicate that the patient may benefit from single site pacing or limited site pacing.

Additionally, the electrical pacing stimulation energy should be optimized to produce cardiac capture. If the pacing stimulation energy is too high, stimulation at multiple pacing sites may cause stress on the heart and the battery life of an implanted device will be needlessly shortened. Also, pacing stimulation energy that is too high may cause unwanted non-cardiac stimulation such as stimulation of the phrenic nerve or stimulation of muscle near the tissue pocket in which the device is implanted. If the pacing stimulation energy is too low, the pacing energy will not evoke a response in the heart and the device will not produce the desired heart contractions.

Multi-site pacing can complicate verification of cardiac capture, which can make it challenging to optimize the pacing stimulation energy for the patient. Knowledge of a patient's cardiac activation propagation pattern can help correctly verify capture. It is therefore desirable for a pacing system to determine the pattern and vectors of propagation of activation of cardiac tissue for the patient for optimization of pacing therapy and verification of capture.

Figure 1:
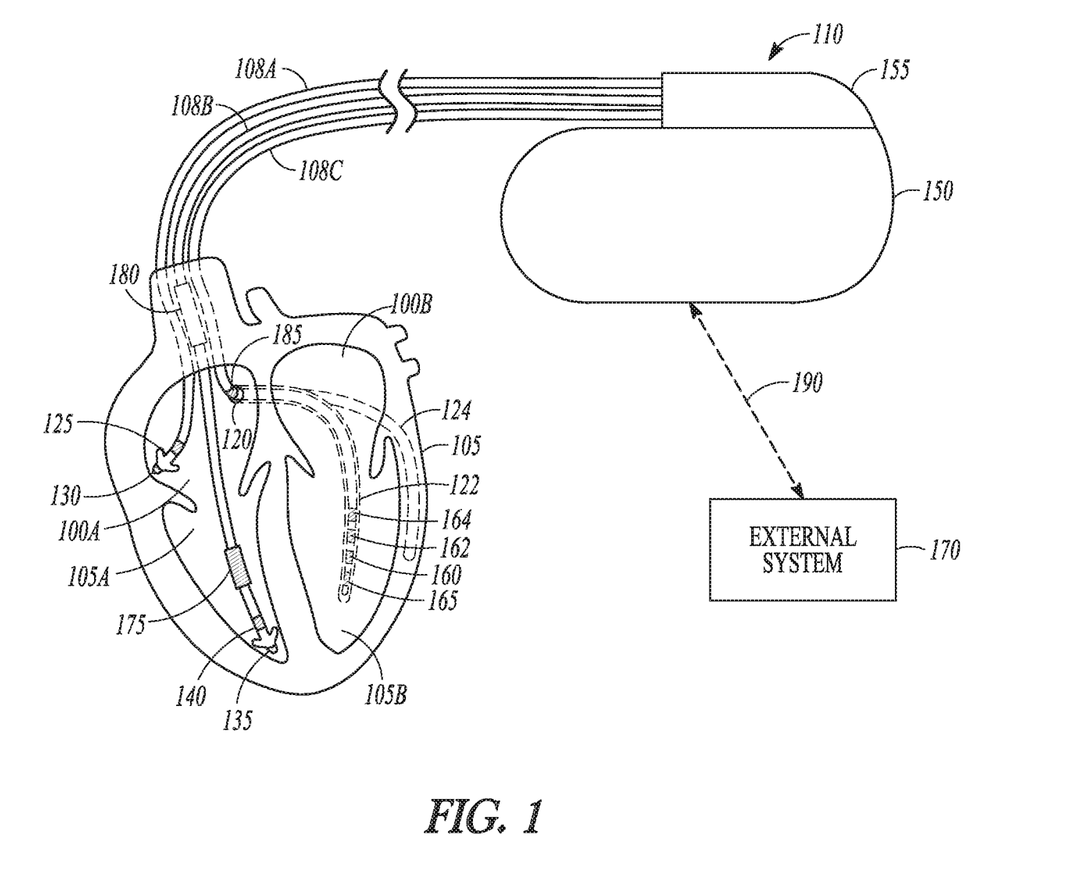
FIG. 1 is an illustration of an example of portions of a system that includes an IMD.

FIG. 1 is an illustration of portions of a system that uses an IMD 110. Examples of IMD 110 include, without limitation, a pacemaker, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals. Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

The IMD 110 can include a third cardiac lead 108C attached to the IMD 110 through the header 155. The third cardiac lead 108C includes electrodes 160, 162, 164, and 165 placed in a coronary vein lying epicardially on the left ventricle (LV) 105B via the coronary vein. The third cardiac lead 108C may include anywhere from two to eight electrodes, and may include a ring electrode 185 positioned near the coronary sinus (CS) 120.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include a mesh including multiple electrodes, patch electrodes, and wireless electrostimulation nodes or "seeds" which can be applied to portions of heart 105.

Figure 2:
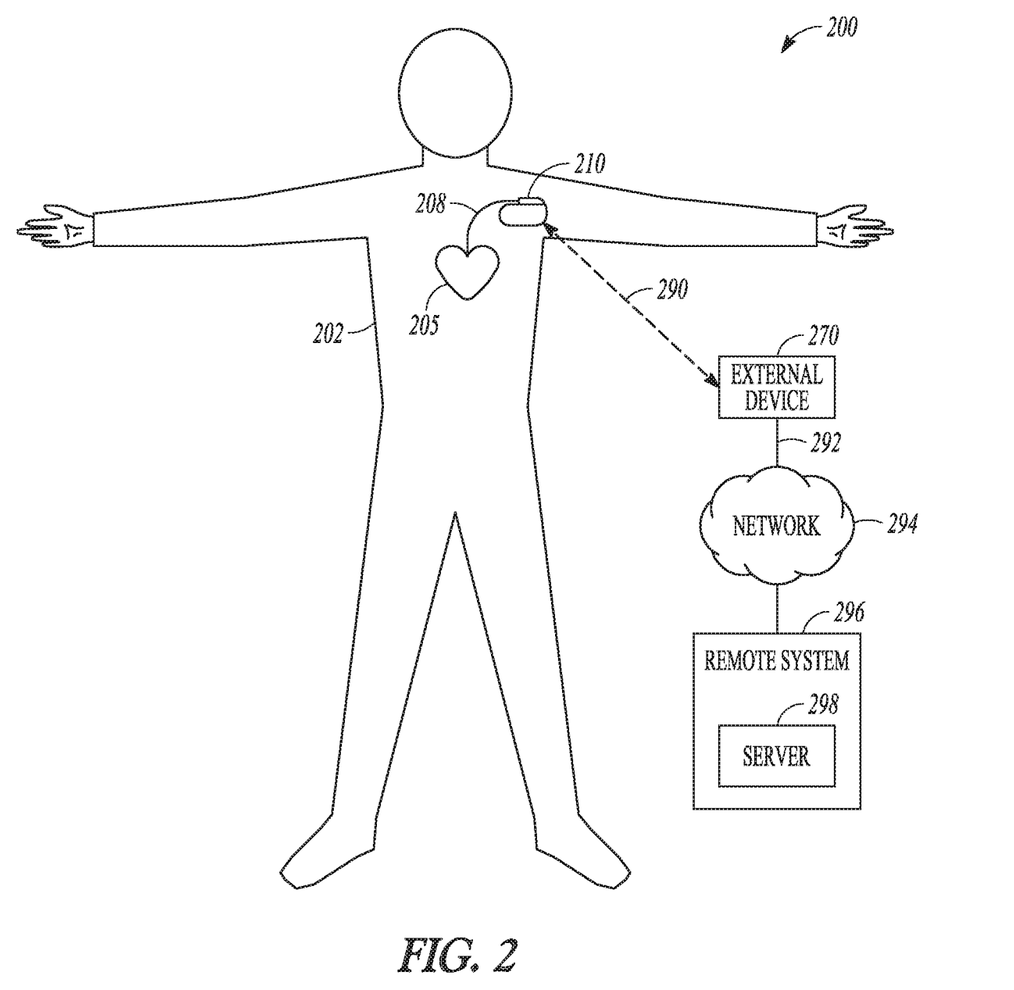
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

Providing pacing energy at an improper pacing site or location can lead to ineffective activation of myocardial tissue. It may be desirable to have an IMD or other medical device automatically run tests to determine the best pacing site or sites, and either propose to the caregiver that these sites be used to provide the pacing therapy or automatically initiate delivery of pacing therapy using a determined optimal pacing configuration.

The multiple electrodes available to the pacing system can be used to determine vectors of activation propagation. The activation vectors include direction information of propagation of activation of cardiac tissue. The activation vectors can be used to provide a map of cardiac activation that can be used to evaluate the activation sequence of the myocardium. Once intrinsic activation propagation is evaluated, pacing therapy can be provided to the patient using patient sites determined using the intrinsic activation. Paced activation vectors can then be sensed and used to "tune" the pacing therapy by adjusting, among other things, pacing sites, the pacing pulse amplitude, the pacing pulse width, and the atrial-ventricular (AV) time delay.

Figure 3:
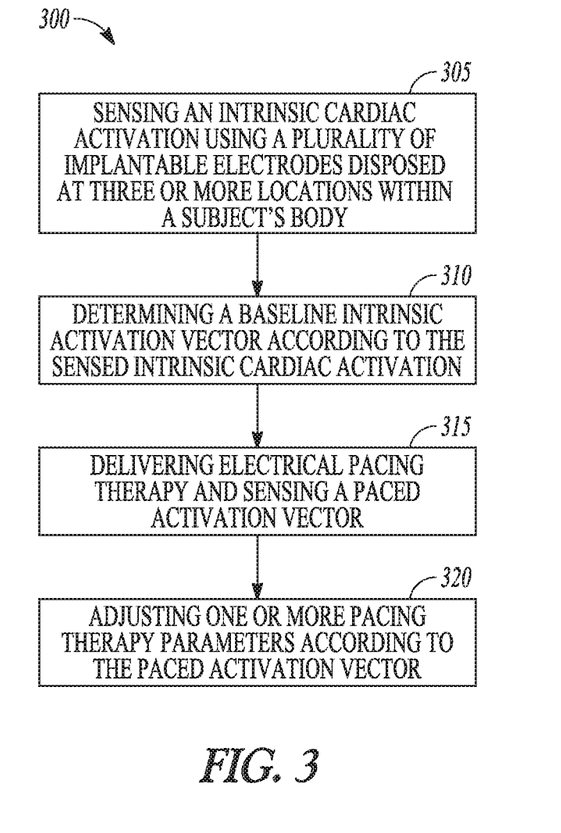
FIG. 3 is a flow diagram of an example of a method of operating a medical device.

FIG. 3 is a flow diagram of an example of a method 300 of operating a medical device or medical device system. At 305, an intrinsic cardiac activation is sensed using multiple implantable electrodes disposed at three or more locations within a subject's body. Sensing the intrinsic cardiac activation may include sensing one or more intrinsic cardiac activation signals. At 310 of FIG. 3, a baseline intrinsic activation vector is determined according to the sensed intrinsic cardiac activation.

In an illustrative example intended to be non-limiting, the baseline intrinsic cardiac activation is sensed using the four LV electrodes 165, 160, 162, and 164 shown in FIG. 1. The intrinsic activation vector can include direction information of the propagation of activation of cardiac tissue within the LV. For instance, if the LV included scar tissue, the propagation pattern may include a "U" shaped pattern around the scar. Sensing with more electrodes would provide better resolution of the intrinsic cardiac activation.

Returning to FIG. 3 at 315, electrical pacing therapy is delivered using the electrodes and a paced activation vector is sensed using the electrodes. At 320, one or more pacing therapy parameters are adjusted according to the sensed paced activation vector, such as by adjusting one or more of the pacing therapy parameters described previously herein.

Figures 4A, 4B:
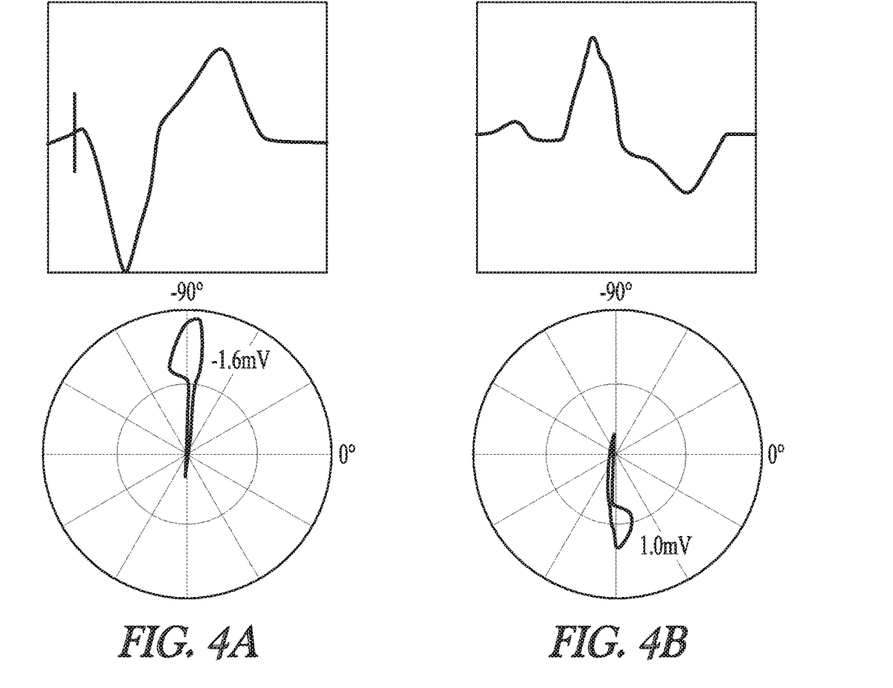
FIGS. 4A-4D illustrate an example of sensing propagation of cardiac tissue activation after delivery of electrical pacing stimulation energy.
Figures 4C, 4D:
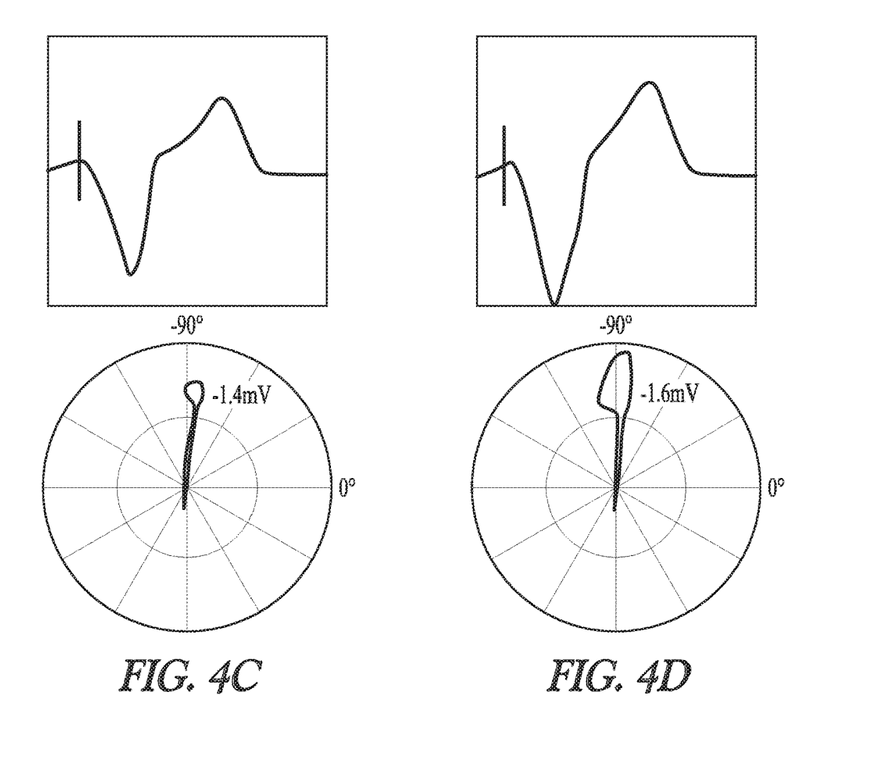

FIGS. 4A-4D illustrate an example of sensing propagation of cardiac tissue activation after delivery of electrical pacing stimulation energy. FIGS. 4A, 4B, 4C, and 4D may correspond to signals sensed at LV electrodes 165, 160, 162, and 164 respectively, of FIG. 1. The paced stimulation energy may be a pace pulse delivered simultaneously to the four locations within the LV as pacing cathodes, and with one or more electrodes of the RV configured as the pacing anode. Each of the illustrations show an electrogram and a vector cardiograph for the sensed activity at the electrode. FIGS. 4A, 4C, and 4D show that the pace pulse induced capture at those locations while FIG. 4B shows that the pace pulse did not induce capture at that location.

From the illustrations, it can be seen that cardiac capture can be determined using one or both of the polarity of the electrogram and the direction information of the vector cardiograph. For instance, a negative polarity of the sensed electrogram signal at an electrode may indicate that the activation wave-front is moving away from the electrode, which indicates capture at the electrode. A positive polarity may indicate that the activation wave-front is moving toward the electrode, which indicates non-capture at the electrodes. The direction information of the vector cardiograph shows the vector included in range of zero degrees to ninety degrees (0° to −90°) indicates capture. Based on the sensed paced activation vector or vectors, one or more electrodes 165, 160, 162, and 164 can be selected for delivering subsequent electrical pacing therapy. Additional parameters (e.g., the pacing pulse amplitude, the pacing pulse width, and the AV time delay) may be adjusted as part of tuning the pacing therapy.

Figure 5:
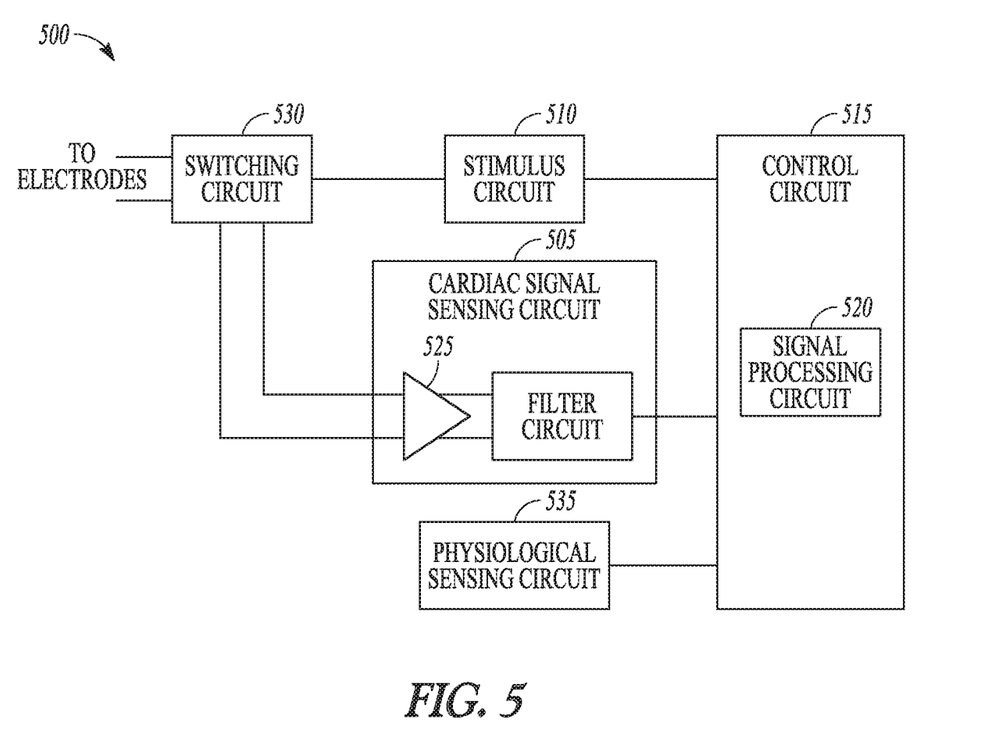
FIG. 5 is a block diagram of portions of an example of a medical device operable to automatically optimize electrical pacing therapy.

FIG. 5 is a block diagram of portions of an example of a medical device 500 operable to automatically optimize electrical pacing therapy. The device 500 includes a cardiac signal sensing circuit 505 that can be electrically coupled to electrodes. The cardiac signal sensing circuit 505 can produce a cardiac signal representative of intrinsic cardiac activation sensed at multiple locations within a patient or subject. The electrodes may be disposed at three or more locations within the patient. In some examples, the electrodes are implantable electrodes that can be disposed within the same heart chamber. In some examples, the electrodes are implantable subcutaneously and can be disposed without direct cardiac contact to the. In some examples, the electrodes are disposed with sufficient separation to provide direction information as a cardiac activation wave-front passes the disposed electrodes.

The medical device 500 also includes a stimulus circuit 510 that provides an electrical cardiac pacing stimulus to the electrodes, and a control circuit 515 electrically coupled to the cardiac signal sensing circuit 505 and the stimulus circuit 510. The control circuit 515 can include a processor such as a microprocessor, a digital signal processor, application specific integrated circuit (ASIC), or other type of processor, interpreting or executing instructions in software modules or firmware modules. In some examples, the control circuit 515 includes a sequencer. A sequencer refers to a state machine or other circuit that sequentially steps through a fixed series of steps to perform one or more functions. The steps are typically implemented in hardware or firmware. The control circuit 515 can include other circuits or sub-circuits to perform the functions described. These circuits may include software, hardware, firmware or any combination thereof. Multiple functions can be performed in one or more of the circuits or sub-circuits as desired.

The medical device 500 also includes a signal processing circuit 520 electrically coupled to the cardiac signal sensing circuit 505. The signal processing circuit 520 determines a baseline intrinsic activation vector according to the sensed intrinsic cardiac activation. The control circuit 515 initiates delivery of electrical pacing therapy to the patient. The control circuit 515 may select one or more tissue sites to deliver the pacing therapy based on the pattern of the intrinsic activation or the intrinsic activation vector. The control circuit 515 initiates sensing of a paced activation vector resulting from the delivery of pacing therapy. The paced activation vector may be sensed using the signal processing circuit 520. Based on the paced activation vector, the control circuit 515 may adjust one or more pacing therapy parameters.

In some examples, the medical device 500 is coupled to four electrodes disposed at four locations within the LV. The control circuit 515 may initiate delivery of a pacing stimulation pulse to all of the LV electrodes simultaneously and sense the result paced activation vector or vectors as described previously in regard to FIG. 4.

In other examples, the control circuit 515 may initiate delivery of a series of pacing pulses using each of the electrodes of the plurality of electrodes in turn as a pacing cathode and the other electrodes of the plurality of electrodes as the pacing anode. For instance, the control circuit 515 may initiate sensing of propagation of intrinsic activation of cardiac tissue using electrode 165 in FIG. 1 as the sensing cathode and electrodes 160, 162, and 164 connected together as the sensing anode. The control circuit 515 may then initiate delivery of a pace pulse with electrode 165 as the pacing cathode and electrodes 160, 162, and 164 as the pacing anode. The control circuit 515 may then immediately sense the pace-induced cardiac activation with electrode 165 as the sensing cathode and electrodes 160, 162, and 164 as the sensing anode. Pacing and sensing may be similarly performed using another LV electrode as the cathode and the remaining electrodes as the anode until each LV electrode has been configured as the pacing/sensing cathode. Pace induced activation may then be determined from the sensed signals.

In further examples, the control circuit 515 may initiate delivery of a series of pacing pulses using each of the electrodes of the plurality of electrodes in turn as a pacing cathode and using an electrode formed on the housing of the medical device or using one or more electrodes located in the RV.

Figure 6:
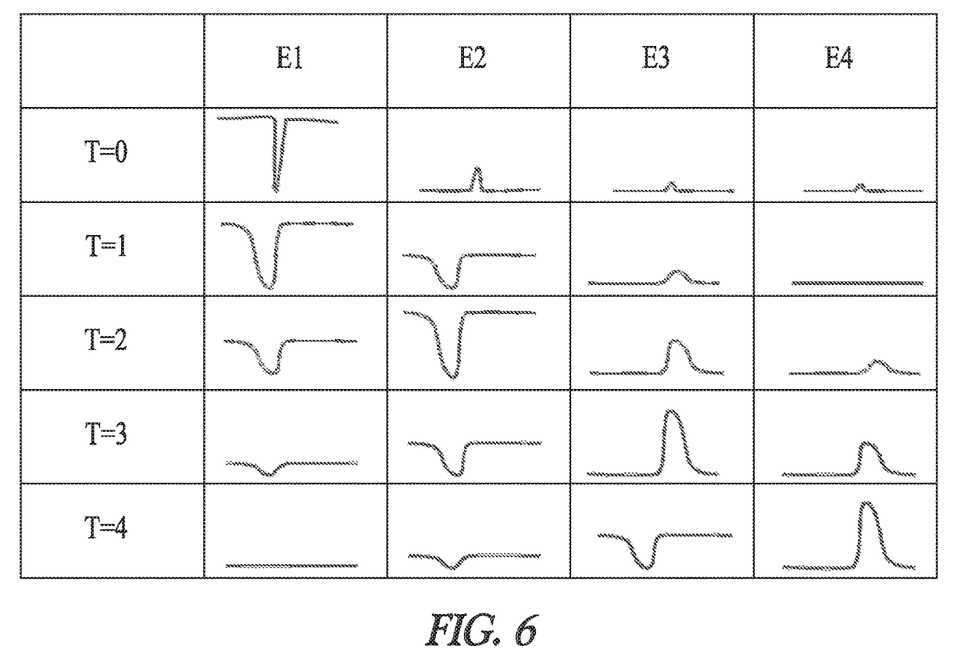
FIG. 6 illustrates another example of sensing propagation of cardiac tissue activation after delivery of electrical pacing stimulation energy.

FIG. 6 illustrates another example of sensing propagation of cardiac tissue activation after delivery of electrical pacing stimulation energy. As an illustrative example, the electrodes E1, E2, E3, and E4 may correspond to LV electrodes 165, 160, 162, and 164, respectively in FIG. 1, and the illustrations may represent pace-induced cardiac activation progressing through the LV. The example of FIG. 6 represents a pace pulse delivered at electrode E1 at time T=0.

If electrode E1 corresponds to electrode 165 in FIG. 1, the activation wave-front progresses from 165 to electrodes 160, 162, and 164 sequentially. Time in FIG. 6 starts at time at time T=0 and progresses to T=4 in the vertical direction. The paced induced cardiac activation is sensed immediately after the pace pulse is provided at T=0, and representations of the cardiac activation at the electrodes is shown in the row corresponding to T=0. The negative polarity of the pulse at electrode E1 indicates capture at electrode E1, and the positive polarity at electrodes E2, E3, E4 indicates the cardiac activation travelling toward the electrodes. The illustrations show cardiac activation occurring at time T=1 at electrode E2, and at electrode E3 at time T=4. The cardiac activation is still travelling toward electrode E4 at time T=4.

Figure 7:
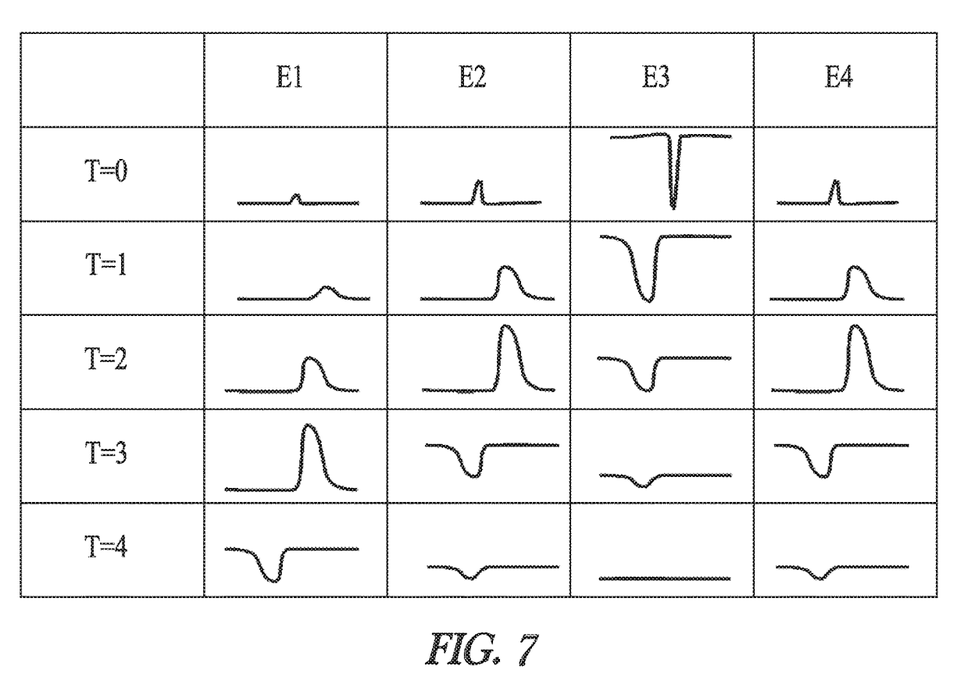
FIG. 7 illustrates still another example of sensing propagation of cardiac tissue activation after delivery of electrical pacing stimulation energy.

FIG. 7 illustrates another example of sensing propagation of cardiac tissue activation after delivery of electrical pacing stimulation energy. It is similar to the example shown in FIG. 6 except that FIG. 7 represents a pace pulse delivered at electrode E3 at time T=0. The Figure illustrates capture at electrode E3 and the progression of the pace induced cardiac activation towards the other electrodes. Cardiac activation occurs at electrodes E2 and E4 near time T=3, and at electrode E1 near time T=4. The paced activation vector can be constructed using the timing information. The pacing therapy can be tuned by changing the pacing therapy parameters and constructing sensed paced activation vectors to monitor the impact of the tuning.

Sensing the paced activation vector following delivery of pacing stimulation can involve challenges. Returning to FIG. 5, the electrodes can be in electrical communication with one or more sense amplifiers 525 included in the cardiac signal sensing circuit 505 to monitor the electrical cardiac activity.

Typically, a blanking period is initiated in association with delivery of an electrostimulation pulse. In some examples, the sense amplifiers are "blanked" during the duration of the pulse by being electrically disconnected or otherwise electrically isolated from the sensing electrodes. After a specified period of time (e.g., forty milliseconds or 40 ms), the sense amplifiers 525 are electrically reconnected to the electrodes. Additionally, there may be a settling time associated with connection and re-connecting sense amplifiers to electrodes. The blanking period prevents the sense amplifiers 525 from being swamped by the electrostimulation energy from the pace pulse.

In some examples, there is a sense amplifier available for each of the sensing cathode/anode pairs used in sensing the activation vectors. In some examples, a first subset of the electrodes may be configured for providing pacing therapy to the patient. The available sense amplifiers may be electrically coupled to the first subset of electrodes. For example, sense amplifiers may normally be electrically coupled to a can electrode and an electrode of the RA, the RV, and one electrode of the LV. The sense amplifiers may be used to sense intrinsic cardiac activation as part of pacing therapy. To sense a paced activation vector, the control circuit 515 may electrically couple the available sense amplifier or amplifiers to a different subset of electrodes (e.g., all LV electrodes) to sense a paced activation vector. The medical device 500 may include a switch circuit 530 to multiplex the sense amplifiers to different electrodes. After the paced activation vector is sensed the sense amplifiers 525 may be re-coupled to the first subset of electrodes.

Figure 8:
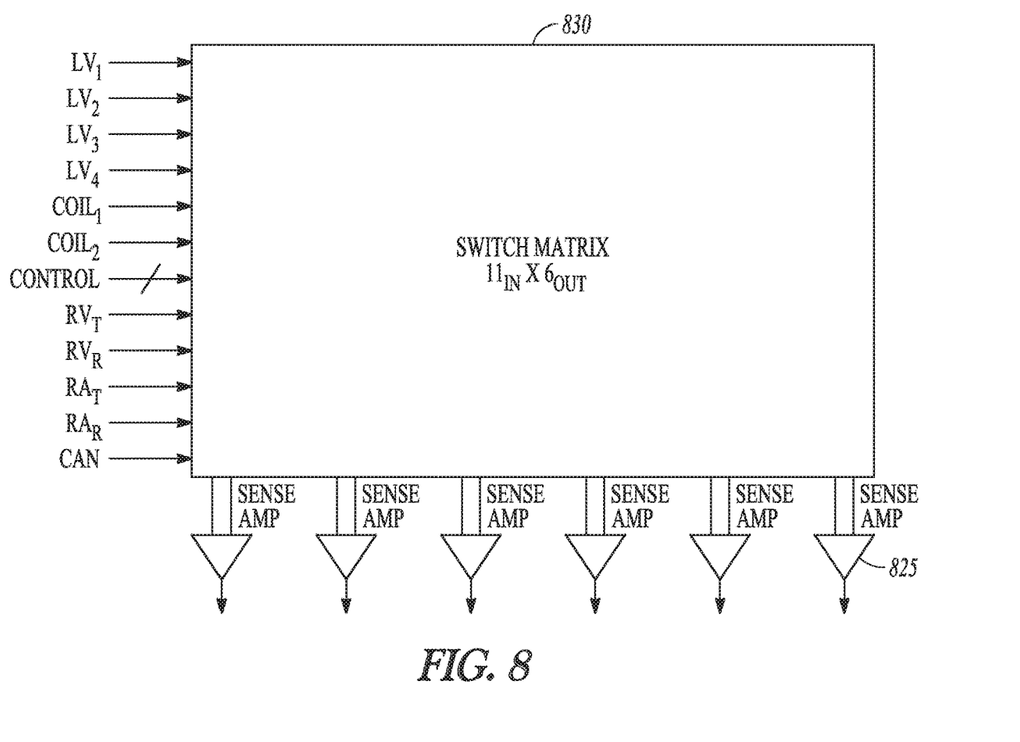
FIG. 8 is a block diagram of an example of a switch matrix circuit 830 and sense amplifier circuits.

FIG. 8 is a block diagram of an example of a switch matrix circuit 830 and sense amplifier circuits 825. The example switch matrix circuit includes eleven inputs that can be coupled to eleven of the electrodes shown in FIG. 1, such as the LV lead electrodes 165, 160, 162, 163, coil electrodes 175, 180, RV tip electrode 135, RV ring electrode 140, RA tip electrode 130, RA ring electrode 125, and a can electrode formed using IMD housing 150. The switch matrix circuit 830 electrically couples the electrodes to the sense amplifiers. If all of the inputs from the electrodes are available for sensing, the switch matrix would be an eleven by six (11×6) matrix.

Depending on the pacing system implemented, there may not be enough sense amplifiers available to obtain signals at multiple locations within a single cardiac cycle to generate an activation vector, whether it is an intrinsic vector a paced vector. Additionally, sensing may be limited due to one or both of the blanking and settling time associated with sense amplifier circuits. In some examples, the activation vector is obtained over multiple cardiac cycles by sensing using only one or two sense amplifiers. The sense amplifiers may be multiplexed to different electrodes for different cardiac cycles to obtain the signals needed to form the activation vector. The results from the multiple cardiac cycles can then be combined to form the activation vector. A signal fiducial may be used to align the sensed cardiac signals for forming the activation vector. For instance, the signal processing circuit 520 may align sensed cardiac signals using an R-wave or P-wave evident in the sensed signals.

As explained previously, sensed intrinsic activation vectors and sensed paced activation vectors can be used to tune the pacing therapy prescribed for a patient. In some examples, the pacing therapy can be adjusted based on a vector template. The signal processing circuit 520 may calculate the correlation of a sensed paced activation vector to a specified paced activation vector template. The calculated correlation may indicate the degree of similarity between sensed paced activation vector and the activation vector template. The control circuit 515 may adjust pacing therapy parameters according to the determined correlation.

For instance, the template may represent the desired or an ideal cardiac activation for the patient. The control circuit 515 may adjust pacing therapy parameters in order for the paced activation vectors to match the paced activation vector template as close as possible, such as by maximizing the calculated correlation. Alternatively, the calculated correlation may reflect the difference between the sensed paced activation vector and the activation vector template. In this case, the control circuit 515 may adjust pacing therapy parameters in order to minimize the calculated correlation and thereby minimize the difference between the sensed paced activation vector and the activation vector template.

In some examples, the ideal cardiac activation can be determined from a timing interval. For instance, the signal processing circuit 520 may identify a first signal fiducial in the sensed intrinsic cardiac activation and a second signal fiducial in the sensed intrinsic cardiac activation, and to determine the time interval between the first and second signal fiducials. As an illustrative example intended to be non-limiting, the signal processing circuit 520 may detect a first signal fiducial indicative of a Q-wave and a second signal fiducial indicative of LV depolarization, and the activation time interval can be the Q-LV time interval. The control circuit 515 may adjust the one or more pacing therapy parameters to meet a specified target time interval between the first and second signal fiducials. In certain examples, the control circuit 515 adjusts the pacing therapy parameters to meet the specified target time interval and to meet a specified direction and magnitude target for the paced activation vector.

According to some examples, the vector information can be combined with information obtained using other sensors to tune the pacing therapy. In some examples, the medical device 500 includes a physiological sensing circuit 535 configured to generate a physiological signal different from a cardiac activation signal. The physiological signal includes hemodynamic status information of the subject. The control circuit 515 adjusts the pacing therapy parameters according to the hemodynamic status information and the paced activation vector.

In some examples, the physiological sensing circuit 535 includes a heart sound sensing circuit (e.g., an accelerometer, or microphone) that produces an electrical heart sound signal representative of mechanical cardiac activity of the patient or subject. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. The heart sound signal produced by the heart sound sensor circuit can be an electrical signal representative of one or more heart sounds.

The medical device 500 may use a parameter measured using the heart sound signal (e.g., heart sound signal amplitude) to quantify the mechanical cardiac contraction. The quantified mechanical cardiac contraction can be used as feedback in addition to the sensed paced activation vector to adjust the pacing therapy. For instance, the control circuit 515 may adjust the pacing parameters to optimize a parameter of the heart sound signal measured by the signal processing circuit 520. For example, the control circuit 515 may select particular parameters that maximizes amplitude of the S1 heart sound for the patient.

In some examples, the physiological sensing circuit 535 includes a blood pressure sensing circuit. In certain examples, the physiological sensing circuit 535 is a pulmonary arterial pressure (PAP) sensing circuit. A PAP sensing circuit may be implanted in a pulmonary artery to sense an electrical PAP signal representative of PAP of the patient. The medical device 500 may use a parameter measured using the PAP signal to quantify the mechanical cardiac contraction of the patient that can be used, in addition to the sensed paced activation vector, to adjust the pacing therapy. For instance, the control circuit 515 may adjust the pacing parameters to optimize a parameter of the PAP signal measured by the signal processing circuit 520.

As explained previously, knowledge of the activation propagation vector can help correctly verify cardiac capture. The medical device 500 can be used to perform a cardiac capture test to determine one or both of an optimized pacing energy and an optimized electrode site or combination of electrode sites to provide the pacing energy.

Figure 9:
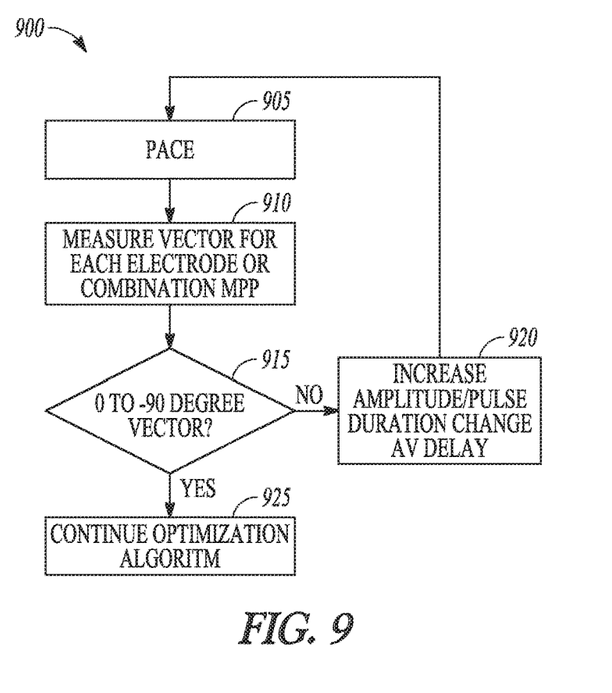
FIG. 9 is a flow diagram of another example of a method of operating a medical device.

FIG. 9 is a flow diagram of a method 900 of operating the medical device 500 to perform a cardiac capture test. At 905, the control circuit 515 initiates the capture test by initiating delivery of a pace pulse. The pace pulse may be delivered using the electrode for activation of a single pacing site, or a combination of the electrodes for multi-site pacing.

At 910, a paced activation vector may be sensed and measured for pacing sites during the capture test. The paced activation vector may be determined by the signal processing circuit 520 as described previously herein.

At 915, it is determined whether a sensed paced activation vector indicates capture. As explained above in regard to FIG. 4, cardiac capture can be determined using one or both of the polarity of the electrogram and the direction information of the vector cardiograph. For instance, the direction information of the sensed paced vector indicates cardiac capture when the vector is included in range of 0° to −90°.

At 920, if capture is not detected the control circuit may change one or more pacing parameter, such as one or more of the pacing amplitude, the pulse duration or pulse width, and the AV delay. Flow returns to 905 where a pace pulse with the adjusted pace parameters is delivered. If capture is detected, flow continues to 925, where the pacing therapy may be further optimized.

The capture test may be performed by delivering pacing energy to all available individual pacing sites and multi-sites, or the capture test may be only run for specified (e.g., programmed) sites or multi-sites. The combinations of electrodes tested may include using each of the electrodes and combinations of the electrodes as a pacing cathode, and using the other as the pacing anode.

The delivery of the pacing energy to a pacing site or multi-site includes delivering a series of pacing pulses of varying pulse energy to the site. The series may include a successive reduction of the energy of the pacing pulses. A first pacing pulse that will likely induce capture is delivered. The energy of subsequent pacing pulses is reduced in steps until the device verifies that failure to induce capture has occurred. Alternatively, the sequence may include increasing the energy of the pacing pulses. A first pacing pulse that is below a threshold likely to induce capture is delivered. The energy of subsequent pacing pulses is increased in steps until the device verifies that capture was induced. When the cardiac capture pulse energy level threshold is determined for the combinations of the electrodes, one or more electrodes of the electrodes can be selected for delivering subsequent electrical pacing therapy according to determined cardiac capture pulse energy level thresholds.

Pacing therapy and the pacing sites used to deliver the therapy should be optimized to provide the most effective device-based therapy. Automaticity simplifies the process in optimizing the therapy, which may result in more caregivers configuring the therapy for their patients. Using cardiac activation direction information (e.g., activation vectors) may take into account specific etiology of the patient's cardiac disease, and this may improve the likelihood of finding the optimal pacing site and therapy parameters for a particular patient.

Returning to FIG. 5, although the functionality is described with respect to one medical device, the functions of the medical device may be performed by multiple devices of a medical device system. In some examples, the signal processing circuit 520 is included in a separate device, such as a pacing system analyzer (PSA). Intrinsic and paced cardiac activation signals may be sensed using an implantable device and the sensed activation signals may be uploaded to the PSA for processing to construct the sensed activation vectors. The PSA may change the pacing parameters by programming to tune the pacing therapy. In some examples, the medical device 500 of FIG. 5 is included in a PSA and the PSA is electrically coupled to leads that include electrodes to perform the functions described that are performable by the medical device 500.

The systems, devices, and methods discussed in this document may improve the medical technology of automated cardiac rhythm management (CRM) and prevention of worsening of cardiac function. Delivering therapy to device-determined optimized pacing sites may also enhance the performance and functionality of an implantable CRM device.

Providing pacing energy at an improper pacing site or location can lead to ineffective activation of myocardial tissue. Knowledge of the activation propagation patterns can be used to determine the optimum pacing sites and help determine the timing of the delivery of the pacing energy pulses of the pacing therapy. Multiple electrodes available to the pacing system can be used to determine vectors of activation propagation. The activation vectors include direction information of propagation of activation of cardiac tissue. The activation vectors can be used to provide a map of cardiac activation that can be used to evaluate the activation sequence of the myocardium. Once intrinsic activation propagation is evaluated, pacing therapy can be provided to the patient using patient sites determined using the intrinsic activation.

Having an IMD or other medical device automatically run tests can determine the best pacing site or sites. The device-determined activation vectors can then be sensed and used to "tune" the pacing therapy by adjusting, among other things, pacing sites, the pacing pulse amplitude, the pacing pulse width, and the atrial-ventricular (AV) time delay. Optimizing the pacing therapy can increase the efficacy of the therapy delivered by the device and improve satisfaction of the patients prescribed the devices.

ADDITIONAL DESCRIPTION AND EXAMPLES

Example 1 can include subject matter (such as an apparatus) comprising: a cardiac signal sensing circuit configured for coupling electrically to a plurality of electrodes and to sense intrinsic cardiac activation at three or more locations within a subject's body using the electrodes; a stimulus circuit configured for coupling to the plurality of electrodes; a signal processing circuit electrically coupled to the cardiac signal sensing circuit and configured to determine a baseline intrinsic activation vector according to the sensed intrinsic cardiac activation, wherein an intrinsic activation vector includes direction information of propagation of activation of cardiac tissue; and a control circuit electrically coupled to the cardiac signal sensing circuit and stimulus circuit and configured to: initiate delivery of electrical pacing therapy using initial pacing parameters determined according to the baseline intrinsic activation vector; initiate sensing of a paced activation vector; and adjust one or more pacing therapy parameters according to the paced activation vector.

In Example 2, the subject matter of Example 1 optionally includes a control circuit configured to initiate delivery of the electrical pacing therapy simultaneously to the three or more locations within a heart chamber, and select one or more electrodes of the plurality of electrodes for delivery of subsequent electrical pacing therapy according to the sensed paced activation vector.

In Example 3, the subject matter of one or both of Examples 1 and 2 optionally includes a control circuit configured to: initiate delivery of a series of pacing pulses using each of the electrodes of the plurality of electrodes in turn as a pacing cathode and the other electrodes of the plurality of electrodes as the pacing anode; initiate sensing paced activation vectors for the pacing pulses; and select one or more electrodes of the plurality of electrodes for delivery of subsequent electrical pacing therapy according to the one or more sensed paced activation vectors.

In Example 4, the subject matter of one or any combination of Examples 1-3 optionally includes a signal processing circuit configured to determine a correlation of a sensed paced activation vector to a specified paced activation vector template, and wherein the control circuit is configured to adjust the one or more pacing therapy parameters according to the determined correlation.

In Example 5, the subject matter of one or any combination of the Examples 1-4 optionally includes a physiologic sensing circuit configured to generate a physiological signal different from a cardiac activation signal, wherein the physiological signal includes hemodynamic status information of the subject, and wherein the control circuit is configured to adjust the one or more pacing therapy parameters according to the hemodynamic status information and the paced activation vector.

In Example 6, the subject matter of one or any combination of Examples 1-5 optionally includes a signal processing circuit configured to identify a first signal fiducial in the sensed intrinsic cardiac activation and a second signal fiducial in the sensed intrinsic cardiac activation; and to determine a time interval between the first and second signal fiducials, and wherein the control circuit is configured to adjust the one or more pacing therapy parameters to meet a specified target time interval between the first and second signal fiducials and to meet a specified direction and magnitude target for the paced activation vector.

In Example 7, the subject matter of one or any combination of Examples 1-6 optionally includes a control circuit configured to: initiate delivery of pacing pulses using combinations of the electrodes that include one electrode of the plurality of electrodes as a pacing cathode and the other electrodes as the pacing anode; initiate sensing paced activation vectors resulting from the pacing pulses; determine a cardiac capture pulse energy level threshold for the electrodes using the sensed paced activation vectors; and select one or more electrodes of the plurality of electrodes for delivering subsequent electrical pacing therapy according to determined cardiac capture pulse energy level thresholds.

In Example 8, the subject matter of one or any combination of Examples 1-6 optionally includes a control circuit configured to: initiate delivery of pacing pulses using combinations of the electrodes as a pacing cathode and the other electrodes as the pacing anode; initiate sensing paced activation vectors resulting from the pacing pulses; and determine a cardiac capture pulse energy level threshold for the combinations of the electrodes using the sensed paced activation vectors; and select one or more electrodes of the plurality of electrodes for delivering subsequent electrical pacing therapy according to determined cardiac capture pulse energy level thresholds.

In Example 9, the subject matter of one or any combination of Examples 1-8 optionally includes a plurality of sense amplifier circuits, wherein the control circuit is configured to electrically couple the sense amplifier circuits to a first subset of the plurality of electrodes to sense the intrinsic cardiac activation, and electrically couple the sense amplifiers to a different subset of the electrodes to sense the paced activation vector.

In Example 10, the subject matter of one or any combination of Examples 1-9 optionally includes a plurality of electrodes, wherein the electrodes are implantable within a heart chamber and wherein the intrinsic activation vector and the paced activation vector include direction information of propagation of activation of cardiac tissue within the heart chamber.

Example 11 can include subject matter (such as a method of operating an ambulatory medical device, a means for performing acts, or a machine-readable medium including instructions that, when performed by the machine, cause the machine to perform acts), or can optionally be combined with the subject matter of one or any combination of Examples 1-10 to include such subject matter, comprising: sensing an intrinsic cardiac activation using a plurality of implantable electrodes disposed at three or more locations within a subject's body; determining a baseline intrinsic activation vector according to the sensed intrinsic cardiac activation, wherein an intrinsic activation vector includes direction information of propagation of activation of cardiac tissue; delivering electrical pacing therapy to the heart chamber using initial pacing parameters determined according to the baseline intrinsic activation vector; sensing a paced activation vector using the plurality of electrodes; and adjusting one or more pacing therapy parameters according to the paced activation vector.

In Example 12, the subject matter of Example 11 optionally includes delivering the electrical pacing therapy simultaneously to three or more locations within a heart chamber, and wherein adjusting one or more pacing therapy parameters includes selecting one or more electrodes of the plurality of electrodes for delivering subsequent electrical pacing therapy according to the sensed paced activation vector.

In Example 13, the subject matter of one or both of Examples 11 and 12 optionally includes delivering a series of pacing pulses using each of the electrodes of the plurality of electrodes in turn as a pacing cathode and the other electrodes of the plurality of electrodes as the pacing anode; sensing paced activation vectors for the pacing pulses; and wherein adjusting one or more pacing therapy parameters includes selecting one or more electrodes of the plurality of electrodes for delivering the electrical pacing therapy according to the sensed paced activation vectors.

In Example 14, the subject matter of one or any combination of Examples 11-13 optionally includes adjusting pacing therapy parameters to minimize a difference between the sensed paced activation vector and a specified paced activation vector template.

In Example 15, the subject matter of one or any combination of Examples 11-14 optionally includes sensing a physiological signal different from a cardiac activation signal, wherein the physiological signal includes hemodynamic status information of the subject, and wherein the adjusting pacing therapy parameters includes adjusting the one or more pacing therapy parameters according to the hemodynamic status information and the paced activation vector.

In Example 16, the subject matter of one or any combination of Examples 11-15 optionally includes identifying a first signal fiducial in the sensed intrinsic cardiac activation and a second signal fiducial in the sensed intrinsic cardiac activation, and wherein the adjusting pacing therapy parameters includes adjusting pacing therapy parameters to meet a specified target time interval between the first and second signal fiducials and to meet a specified direction and magnitude target for the paced activation vector.

In Example 17, the subject matter of one or any combination of Examples 11-16 optionally includes: delivering pacing pulses using combinations of the electrodes, wherein the combinations include using each of the electrodes of the plurality of electrodes and combinations of the electrodes as a pacing cathode and the other electrodes of the plurality of electrodes as the pacing anode; sensing paced activation vectors resulting from the pacing pulses; and determining a cardiac capture pulse energy level threshold for the combinations of the electrodes using the sensed paced activation vectors, and wherein adjusting one or more pacing therapy parameters includes selecting one or more electrodes of the plurality of electrodes for delivering subsequent electrical pacing therapy according to determined cardiac capture pulse energy level thresholds.

Example 18 can include subject matter (such as an apparatus), or can optionally be combined with the subject matter of one or any combination of Examples 1-17 to include such subject matter, comprising: a cardiac signal sensing circuit configured for coupling to a plurality of electrodes and configured to sense a cardiac activation signal at each of three or more locations within a heart chamber of a subject; a stimulus circuit configured for coupling to the plurality of electrodes and configured to provide electrical pacing stimulation energy to the electrodes; a signal processing circuit electrically coupled to the cardiac signal sensing circuit and configured to determine an activation vector according to the sensed cardiac activation signals, wherein an activation vector includes direction information of propagation of activation of cardiac tissue; and a control circuit electrically coupled to the cardiac signal sensing circuit and stimulus circuit and configured to: initiate delivery of pacing pulses using combinations of the electrodes, wherein the combinations include using each of the electrodes of the plurality of electrodes and combinations of the electrodes as a pacing cathode and the other electrodes of the plurality of electrodes as the pacing anode; initiate sensing of paced activation vectors resulting from the pacing pulses; determine a cardiac capture pulse energy level threshold for the combinations of the electrodes using the sensed paced activation vectors; and select one or more electrodes of the plurality of electrodes for delivering subsequent electrical pacing therapy according to determined cardiac capture pulse energy level thresholds.

In Example 19, the subject matter of Example 18 optionally includes a control circuit configured to detect cardiac capture using the direction information of the paced activation vectors.

In Example 20, the subject matter of one or both of Examples 18 and 19 optionally include a plurality of sense amplifier circuits and a switching matrix circuit; wherein the control circuit is configured to: electrically couple, using the switching matrix circuit, the sense amplifier circuits to a first subset of the plurality of electrodes to deliver the pacing pulses; and electrically couple the sense amplifier circuits to a second subset of electrodes to sense the paced activation vectors.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a cardiac signal sensing circuit configured for coupling electrically to a plurality of electrodes and to sense intrinsic cardiac activation at three or more locations associated with a left ventricle of a subject using the electrodes;
   a stimulus circuit configured for coupling to the plurality of electrodes and to deliver electrical pacing therapy to the left ventricle;
   a signal processing circuit electrically coupled to the cardiac signal sensing circuit and configured to determine a baseline intrinsic activation vector according to the sensed intrinsic cardiac activation, wherein an intrinsic activation vector includes direction information of propagation of activation of cardiac tissue; and a control circuit electrically coupled to the cardiac signal sensing circuit and stimulus circuit and configured to: initiate delivery of the electrical pacing therapy using initial pacing parameters determined according to the baseline intrinsic activation vector; initiate sensing of a paced activation vector; and adjust one or more pacing therapy parameters according to the paced activation vector.

2. The apparatus of claim 1, wherein the control circuit is configured to initiate delivery of the electrical pacing therapy simultaneously to the three or more locations associated with the left ventricle, and select one or more electrodes of the plurality of electrodes for delivery of subsequent electrical pacing therapy according to the sensed paced activation vector.

3. The apparatus of claim 1, wherein the control circuit is configured to:
initiate delivery of a series of pacing pulses using each of the electrodes of the plurality of electrodes in turn as a pacing cathode and the other electrodes of the plurality of electrodes as the pacing anode;
initiate sensing paced activation vectors for the pacing pulses; and
select one or more electrodes of the plurality of electrodes for delivery of subsequent electrical pacing therapy according to the one or more sensed paced activation vectors.

4. The apparatus of claim 1, wherein the signal processing circuit is further configured to determine a correlation of a sensed paced activation vector to a specified paced activation vector template, and wherein the control circuit is configured to adjust the one or more pacing therapy parameters according to the determined correlation.

5. The apparatus of claim 1, including a physiologic sensing circuit configured to generate a physiological signal different from a cardiac activation signal, wherein the physiological signal includes hemodynamic status information of the subject, and wherein the control circuit is configured to adjust the one or more pacing therapy parameters according to the hemodynamic status information and the paced activation vector.

6. The apparatus of claim 1, wherein the signal processing circuit is configured to identify a first signal fiducial in the sensed intrinsic cardiac activation and a second signal fiducial in the sensed intrinsic cardiac activation; and to determine a time interval between the first and second signal fiducials, and wherein the control circuit is configured to adjust the one or more pacing therapy parameters to meet a specified target time interval between the first and second signal fiducials and to meet a specified direction and magnitude target for the paced activation vector.

7. The apparatus of claim 1, wherein the control circuit is configured to:
initiate delivery of pacing pulses using combinations of the electrodes that include one electrode of the plurality of electrodes as a pacing cathode and the other electrodes as the pacing anode;
initiate sensing paced activation vectors resulting from the pacing pulses;
determine a cardiac capture pulse energy level threshold for the electrodes using the sensed paced activation vectors; and select one or more electrodes of the plurality of electrodes for delivering subsequent electrical pacing therapy according to determined cardiac capture pulse energy level thresholds.

8. The apparatus of claim 1, wherein the control circuit is configured to:
initiate delivery of pacing pulses using combinations of the electrodes as a pacing cathode and the other electrodes as the pacing anode;
initiate sensing paced activation vectors resulting from the pacing pulses; and
determine a cardiac capture pulse energy level threshold for the combinations of the electrodes using the sensed paced activation vectors; and
select one or more electrodes of the plurality of electrodes for delivering subsequent electrical pacing therapy according to determined cardiac capture pulse energy level thresholds.

9. The apparatus of claim 1, including a plurality of sense amplifier circuits, wherein the control circuit is configured to electrically couple the sense amplifier circuits to a first subset of the plurality of electrodes to sense the intrinsic cardiac activation, and electrically couple the sense amplifiers to a different subset of the electrodes to sense the paced activation vector.

10. The apparatus of claim 1, including the plurality of electrodes, wherein the electrodes are implantable within a heart and wherein the intrinsic activation vector and the paced activation vector include direction information of propagation of activation of cardiac tissue within the left ventricle of the heart.

11. An automated method of operation of a medical device system, the method comprising:
sensing an intrinsic cardiac activation using a plurality of implantable electrodes disposed at three or more locations associated with a left ventricle of a subject;
determining a baseline intrinsic activation vector according to the sensed intrinsic cardiac activation, wherein an intrinsic activation vector includes direction information of propagation of activation of cardiac tissue;
delivering electrical pacing therapy to the left ventricle using the plurality of implantable electrodes and using initial pacing parameters determined according to the baseline intrinsic activation vector;
sensing a paced activation vector using the plurality of electrodes; and
adjusting one or more pacing therapy parameters according to the paced activation vector.

12. The method of claim 11, wherein delivering electrical pacing therapy includes delivering the electrical pacing therapy simultaneously to three or more locations associated with the left ventricle, and wherein adjusting one or more pacing therapy parameters includes selecting one or more electrodes of the plurality of electrodes for delivering subsequent electrical pacing therapy according to the sensed paced activation vector.

13. The method of claim 11, wherein delivering electrical pacing therapy to the left ventricle includes: delivering a series of pacing pulses using each of the electrodes of the plurality of electrodes in turn as a pacing cathode and the other electrodes of the plurality of electrodes as the pacing anode; sensing paced activation vectors for the pacing pulses; and wherein adjusting one or more pacing therapy parameters includes selecting one or more electrodes of the plurality of electrodes for delivering the electrical pacing therapy according to the sensed paced activation vectors.

14. The method of claim 11, wherein the adjusting pacing therapy parameters includes adjusting pacing therapy parameters to minimize a difference between the sensed paced activation vector and a specified paced activation vector template.

15. The method of claim 11, including sensing a physiological signal different from a cardiac activation signal, wherein the physiological signal includes hemodynamic status information of the subject, and wherein the adjusting pacing therapy parameters includes adjusting the one or more pacing therapy parameters according to the hemodynamic status information and the paced activation vector.

16. The method of claim 11, including identifying a first signal fiducial in the sensed intrinsic cardiac activation and a second signal fiducial in the sensed intrinsic cardiac activation, and wherein the adjusting pacing therapy parameters includes adjusting pacing therapy parameters to meet a specified target time interval between the first and second signal fiducials and to meet a specified direction and magnitude target for the paced activation vector.

17. The method of claim 11, wherein delivering electrical pacing therapy to the left ventricle includes:
   delivering pacing pulses using combinations of the electrodes, wherein the combinations include using each of the electrodes of the plurality of electrodes and combinations of the electrodes as a pacing cathode and the other electrodes of the plurality of electrodes as the pacing anode;
   sensing paced activation vectors resulting from the pacing pulses; and
   determining a cardiac capture pulse energy level threshold for the combinations of the electrodes using the sensed paced activation vectors, and wherein adjusting one or more pacing therapy parameters includes selecting one or more electrodes of the plurality of electrodes for delivering subsequent electrical pacing therapy according to determined cardiac capture pulse energy level thresholds.

18. An apparatus comprising:
   a cardiac signal sensing circuit configured for coupling to a plurality of electrodes and configured to sense a cardiac activation signal at each of three or more locations associated with a left ventricle of a subject using the electrodes;
   a stimulus circuit configured for coupling to the plurality of electrodes and configured to provide electrical pacing stimulation energy to the left ventricle using the electrodes;
   a signal processing circuit electrically coupled to the cardiac signal sensing circuit and configured to determine an activation vector according to the sensed cardiac activation signals, wherein an activation vector includes direction information of propagation of activation of cardiac tissue; and
   a control circuit electrically coupled to the cardiac signal sensing circuit and stimulus circuit and configured to:
      initiate delivery of pacing pulses using combinations of the electrodes, wherein the combinations include using each of the electrodes of the plurality of electrodes and combinations of the electrodes as a pacing cathode and the other electrodes of the plurality of electrodes as the pacing anode;
      initiate sensing of paced activation vectors resulting from the pacing pulses;
      determine a cardiac capture pulse energy level threshold for the combinations of the electrodes using the sensed paced activation vectors; and
      select one or more electrodes of the plurality of electrodes for delivering subsequent electrical pacing therapy according to determined cardiac capture pulse energy level thresholds.

19. The apparatus of claim 18, wherein the control circuit is configured to detect cardiac capture using the direction information of the paced activation vectors.

20. The apparatus of claim 18, including a plurality of sense amplifier circuits and a switching matrix circuit; wherein the control circuit is configured to: electrically couple, using the switching matrix circuit, the sense amplifier circuits to a first subset of the plurality of electrodes to deliver the pacing pulses; and electrically couple the sense amplifier circuits to a second subset of electrodes to sense the paced activation vectors.

* * * * *